United States Patent [19]

Stillabower

[11] Patent Number: 5,411,478
[45] Date of Patent: May 2, 1995

[54] ANGIOPLASTY APPARATUS AND PROCESS

[75] Inventor: Michael E. Stillabower, 1211 Barley Mill Rd., Wilmington, Del. 19807

[73] Assignee: Michael E. Stillabower, Wilmington, Del.

[21] Appl. No.: 89,187

[22] Filed: Jul. 12, 1993

[51] Int. Cl.⁶ .................................... A61M 29/00
[52] U.S. Cl. ............................ 604/96; 606/194; 606/198; 604/104; 604/280
[58] Field of Search ............... 604/104, 96, 281, 280, 604/8, 105; 606/159, 191–194, 198, 108; 623/1, 12, 13

[56] References Cited

U.S. PATENT DOCUMENTS

| | | | |
|---|---|---|---|
| Re. 33,561 | 3/1991 | Levy | 604/96 |
| 4,484,579 | 11/1984 | Meno et al. | 606/194 |
| 4,793,348 | 12/1988 | Palmaz | 606/1 |
| 4,893,623 | 1/1990 | Rosenbluth | 604/104 |
| 4,921,484 | 5/1990 | Hillstead | 606/159 |
| 5,104,404 | 4/1992 | Wolff | 623/1 |
| 5,143,093 | 9/1992 | Sahota | 604/96 |
| 5,196,024 | 3/1993 | Barath | 606/159 |
| 5,221,261 | 6/1993 | Termin et al. | 604/104 |
| 5,269,802 | 12/1993 | Garber | 604/8 |

OTHER PUBLICATIONS

Yazdanfar et al.; Parallel Angioplasty Dilatation Catheter and Guidewire: A New Technique for the Dilatation of Calcified Coronary Arteries; Catheterization and Cardiovascular Diagnosis 28:72–75 (1993).

*Primary Examiner*—C. Fred Rosenbaum
*Assistant Examiner*—Ronald K. Stright, Jr.
*Attorney, Agent, or Firm*—Donald W. Huntley

[57] ABSTRACT

Improvement in balloon angioplasty is realized by a plurality of longitudinal force focusing means around the balloon.

9 Claims, 1 Drawing Sheet

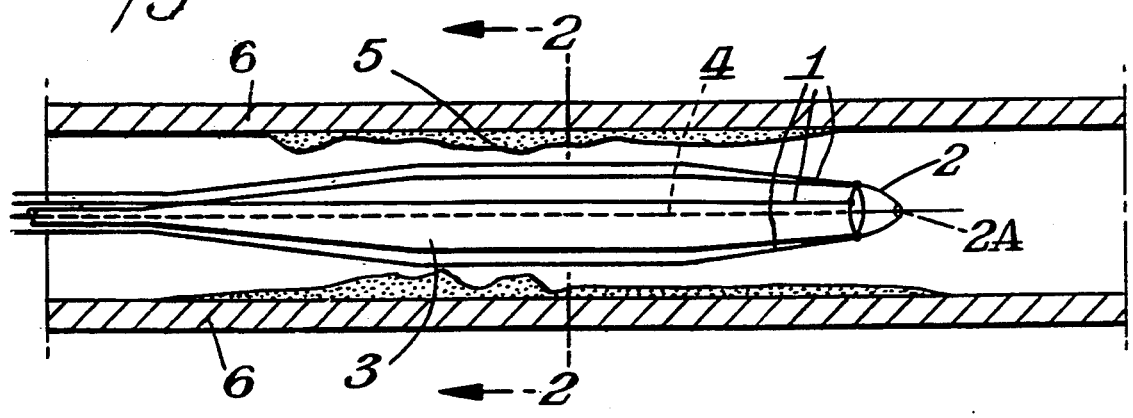
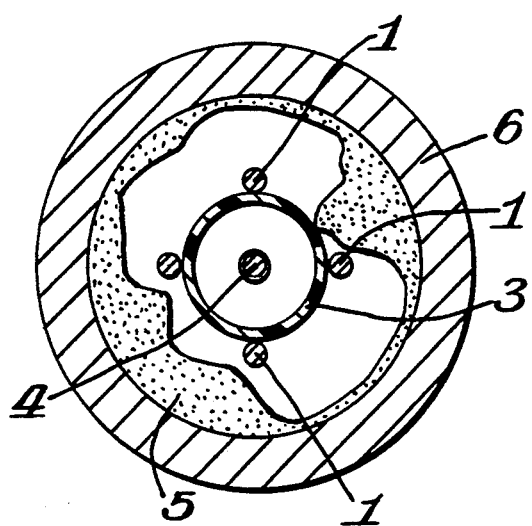
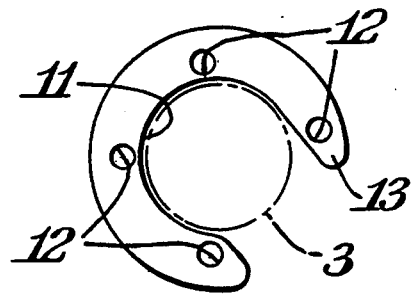

ANGIOPLASTY APPARATUS AND PROCESS

BACKGROUND OF INVENTION

Arteriosclerosis has long been a serious cardiovascular problem, involving the accumulation of deposits or plaque on the interior walls of blood vessels, primarily arteries. Accumulation of such plaque can result in areas of the blood vessel in which a significant portion of the flow is blocked. Such significant blockage is characterized as a stenosis, which causes reduced flow through the blood vessel.

In the past, serious stenoses could generally be alleviated only by bypassing of the blood vessel. More recently, angioplasty techniques were developed to open stenoses in arteries. In such techniques, a balloon catheter is typically inserted in the blood vessel, and the balloon is positioned at the site of the stenosis. Upon inflation, the balloon presses radially on deposited plaque at the site and on the blood vessel wall behind the plaque. Plaque deposits are often irregular in transverse cross-section. Thick portions interfere with the uniform expansion of the balloon, and are, in their composition, non-uniform. These considerations increase the possibility of damage to the artery walls. It has previously been suggested to use a guide wire outside of and parallel to a catheter balloon to produce a crack in heavily calcified plaque, giving improved results and larger openings with less pressure and damage. Such techniques were previously used when normal balloon pressure did not satisfactorily dilate the vessel.

Still other techniques for improving angioplasty treatment include the suggestion of longitudinal cutting strips fastened on the balloon wall. Expansion of the balloon forces these edges outward radially to cut into the plaque. Such cutting edges seriously reduce the flexibility of the balloon, and increase the crossing profile. These features impose limitations on the ability to position the device in tortuous vessels.

Still other improvements in angioplasty techniques involved the balloon itself, providing balloons with improved burst pressure and strength characteristics balanced such that a balloon, if failure occurred, would burst in the longitudinal or axial direction as opposed to the transverse direction, facilitating removal under such circumstances.

A continuing need exists for angioplasty apparatus and techniques that balance the effective opening of the stenosis, minimal damage to the wall of the blood vessel, and minimization of the reformation of the stenosis after completion of the angioplasty.

SUMMARY OF INVENTION

The present invention provides an improvement in angioplasty techniques using balloon catheters which improves the efficiency and safety of the procedure and, in addition, tends to inhibit restenosis or subsequent build up of plaque.

Specifically, the instant invention provides, in an angioplasty apparatus comprising a balloon catheter for applying radial pressure to an arterial stenosis, the improvement wherein the apparatus further comprises at least two longitudinal force distributing means positioned radially exterior to the balloon.

The invention further provides an improved process for balloon angioplasty in which a balloon catheter is inserted into an artery, the balloon is positioned at the site of a stenosis, and the balloon expanded to increase the size of the channel through the stenosis, the improvement comprising positioning at least two force focusing means radially exterior to the balloon prior to inflating the balloon.

BRIEF DESCRIPTION OF THE DRAWINGS

FIG. 1 is a longitudinal cross sectional illustration of the apparatus of the present invention, shown in position at a stenosis in an artery.

FIG. 2 is a transverse cross sectional illustration of the apparatus of the present invention taken at 2—2 of FIG. 1.

FIG. 3 is a planar illustration of a spacer that can be used in the present invention for positioning the force focusing means.

DETAILED DESCRIPTION OF THE INVENTION

The present invention can be used with a wide variety of balloon catheters that have previously been developed for use with balloon angioplasty. Such catheters include, for example, those described in Danforth U.S. Pat. No. 4,881,547, Buchbinder U.S. Pat. No. 5,114,414, and Sahota U.S. Pat. No. 5,143,093, each of which is hereby incorporated by reference. A wide variety of materials can be used for the balloons within such catheter devices. One particularly advantageous material is that described in Levy, U.S. Pat. No. Re. 33,561, also hereby incorporated by reference.

In accordance with the present invention, at least two longitudinal force focusing means are positioned radially exterior to and coaxially with the balloon catheter. The force focusing means focuses the radial pressure of the balloon and, at the same time, distributes the force longitudinally. The force focusing means can be in the form of wires, and can be prepared from any substantially non-toxic or medically non-reactive materials, generally the same metal and metal alloys used in the construction of angioplasty guide wires. In general, stainless steel and other ferrous alloys are particularly satisfactory, and are accordingly preferred.

If the force focusing means are in the form of a wire, a substantially round cross-sectional configuration is generally used. The diameter of the wires can vary substantially, depending on the particular blood vessel in which the stenosis is found and the size of the remaining lumen within the blood vessel. However, for round wires, a diameter of about 0.25-0.50 mm is generally used. To facilitate insertion and positioning, the ends of the wires can be tapered.

In accordance with the present invention, at least two longitudinal force focusing means are used. Typically, these will be uniformly spaced circumferentially around the balloon. However, in an alternative embodiment of the invention, particularly if an asymmetric stenosis is being treated, a greater number of the force focusing means can be positioned adjacent to the thickest part of the stenosis. In general, little additional benefit is attained with more than four force focusing means.

The force focusing means can be placed in position by separate insertion, as previously done for guide wires with balloon angioplasty techniques. Guide wire exchange catheters can also be used to position the elements of the present apparatus. The force focusing means can also be simultaneously inserted through the blood vessel lumen. This can be done by embedding the distal ends of the force focusing means in a thimble. The thimble can be used in conjunction with conventional catheter guidewires running through the center of the thimble. In the alternative, the force focusing means can be inserted after insertion of the balloon itself.

The invention can be more fully understood by reference to the drawings, in which FIG. 1 is a longitudinal cross-sectional illustration of an apparatus of the present invention wherein longitudinal force focusing means (1) are attached, at their distal ends, to a harness or thimble (2), having a central aperture 2A. The thimble can be made, for example, of a soft thermoplastic or elastomeric material. A balloon catheter (3) is positioned within the force focusing means, along a guide wire (4) running through the center of the balloon. The balloon and the force focusing means are all positioned within the lumen defined by stenosis (5) on the interior wall of artery (6). On inflation of the balloon, the force focusing means press into the wall of the stenosis, displacing or fracturing the plaque. Depending on the physical properties of the plaque, it may be cracked, scored, or displaced to permit expansion of the lumen.

FIG. 2 is a transverse cross-sectional illustration of the apparatus of FIG. 1, taken at section 2—2 of FIG. 1.

The positioning of the force focusing means can be facilitated by a spacer as illustrated in FIG. 3. The spacer, which can be inserted either simultaneously with or after the balloon itself, has a central aperture (11) for positioning the balloon catheter and the guide wire, and peripheral apertures (12) for positioning the force focusing means. Thus, the central shaft of the catheter and the guide wire are inserted into the central aperture, having retaining tab (13) retain these components in place once inserted into the spacer. Similarly, the force focusing means are inserted through peripheral spacing apertures (12) so as to position these elements as desired around the balloon and in consideration of the configuration and positioning of the stenosis. The positioning of the spacer is facilitated by a shaft or tether 14, attached to the body of the spacer Positioning of the catheter and the force focusing means can be done with the aid of conventional angiography equipment. On the basis of the information obtainable by such equipment, the cardiologist can select a wire pattern and positions such that the force focusing means are positioned at the point of greatest lumen encroachment. Thus, based on the information available, the force focusing means can be spaced evenly around the lumen or adjusted in a pattern such that they are concentrated on the side of the balloon in which the heaviest deposit of plaque is found.

The surfaces of a force focusing means should be substantially free from sharp edges. This minimizes potential damage to arterial walls and, by either distributing the plaque or fracturing the plaque by deformation, minimizes restenosis after the angioplasty.

The ideal application of the apparatus of the present invention is dependent on individual vessel and stenosis characteristics. Depending on vessel size and stenosis or lesion severity, one or more wires will be positioned across the stenosis using a positioning mechanism. The positioning of the balloon, if desired, can be done simultaneously with the positioning of the force focusing means. Once the desired initial arrangement of components is made, an initial balloon inflation will be performed. The present invention can permit relatively low pressures and a relatively small number of inflations to produce significant increases in luminal cross section area. Depending on the response to the initial arrangement of the apparatus components, further inflations with a larger balloon may be desirable, or a change in the number or positioning of the force distributing means, or all of the above. The present invention causes plaque deformation to occur preferentially in longitudinal lines, coaxially with the vessel lumen, and allows the resilient portions of the artery to stretch after the plaque weakening has been created with the force distributing means.

While the advantages of the present invention are not fully understood, it is believed that the longitudinal force focusing means, by simultaneously focusing the radial force of the balloon and distributing it in a longitudinal direction, permit fracture or redistribution of the stenosis with minimal damage to the artery wall. With a stenosis or accumulated plaque that does not fracture during treatment, the longitudinal distribution of the balloon force can limit the restenosis process, in that any restenosis occurring after the angioplasty may be concentrated in the groves formed by the longitudinal force focusing means during inflation of the balloon. The instant invention thus provides a means for limiting the damage caused by balloon inflation to the channels of the artery coaxial to the artery lumen, and concentrates restenosis to smaller segments of the arterial wall.

The present invention is further illustrated by the following specific example.

EXAMPLE

After selecting a coronary artery stenosis appropriate for balloon dilatation, an angioplasty guide catheter is selected and used to intubate the proximal vessel. The stenosis is crossed with a 0.014 inch High Torque Floppy (ACS) guide wire of coated stainless steel. Three force focusing means in the form of 0.014 inch Standard guide wires (USCI) are delivered across the stenosis over the previously placed 0.014 inch High Torque Floppy guide wire. A standard angioplasty balloon is advanced to the lesion over the initially placed guide wire. A balloon size is selected to be 0.5 to 0.75 mm less than the presumptive normal vessel diameter at the stenosis site. After balloon positioning, a series of inflations is performed with pressures kept in the range of two to six atmospheres. When post inflation angiography suggests suitable lumen caliber has been achieved, the focusing wires are withdrawn and another angiographic visualization of the stenotic area is made with the original guide wire still in place. If results are acceptable, this wire is then removed. Otherwise different balloon size and/or inflation strategy is used depending on the vascular anatomy present.

Over a six month period, the restenosis is observed to be lower than typical for conventional balloon angioplasty treatment without the longitudinal wires.

I claim:

1. In an angioplasty apparatus comprising a balloon catheter for applying radial pressure to a vascular stenosis, and extending at least from a point of insertion to the stenosis, the improvement wherein the apparatus further comprises at least two longitudinal force focusing wires having a substantially circular cross section, each wire having a proximal and a distal end, the proximal end of each wire extending proximal to the balloon catheter and the wires positioned radially exterior to the balloon.

2. An apparatus of claim 1 wherein the distal ends of the force focusing wires are joined to a harness.

3. An apparatus of claim 2 wherein the diameter of the wires is about from 0.25 to 0.50 mm.

4. An apparatus of claim 1 comprising from two to four longitudinal force focusing wires.

5. An apparatus of claim 4 comprising three force focusing means wires.

6. An apparatus of claim 1 wherein the force focusing wires are equally spaced around the circumference of the balloon.

7. An apparatus of claim 1 wherein the force focusing wires are asymmetrically spaced around the circumference of the balloon.

8. In an angioplasty apparatus comprising a balloon catheter for applying radial pressure to a vascular stenosis, and extending at least from a point of insertion to the stenosis, the improvement wherein the apparatus further comprises at least two longitudinal force focusing wires having a substantially circular cross section, each wire having a proximal and a distal end, the proximal end of each wire extending proximal to the balloon catheter and the wires positioned radially exterior to the balloon and further comprising a substantially circular spacer having a central aperture adapted to receive a balloon catheter shaft and an angioplasty guide wire and circumferential apertures adapted to receive the longitudinal force focusing wires.

9. In a process for balloon angioplasty in which a balloon catheter is inserted into an artery, the balloon positioned at the site of a stenosis, and the balloon expanded to increase the size of the channel through the stenosis, the improvement comprising positioning, radially exterior to the balloon prior to inflating the balloon, at least two longitudinal force focusing wires having a substantially circular cross-section, each wire having a proximal and a distal end, the proximal end of each wire extending proximal to the balloon catheter.

* * * * *